United States Patent
Huber et al.

[11] Patent Number: 6,135,269
[45] Date of Patent: Oct. 24, 2000

[54] DRIVE ROLLER UNIT

[75] Inventors: Thomas Huber, Iffeldorf; Martin Dürrwaechter, Irschenberg; Matthias Urch, Poing; Benedikt Kieser, Miesbach, all of Germany

[73] Assignee: Telair International GmbH, Hausham, Germany

[21] Appl. No.: 09/253,590

[22] Filed: Feb. 22, 1999

[30] Foreign Application Priority Data

Feb. 20, 1998 [DD] German Dem. Rep. .......... 198 07 230

[51] Int. Cl.⁷ ..................................................... B65G 43/00
[52] U.S. Cl. ........................... 198/718; 198/722; 198/782
[58] Field of Search .................... 198/722, 718, 198/782, 244, 781.05, 781.06

[56] References Cited

U.S. PATENT DOCUMENTS

| | | |
|---|---|---|
| 2,944,297 | 7/1960 | Maynard . |
| 3,447,665 | 6/1969 | Egeland et al. . |
| 3,712,454 | 1/1973 | McKee . |
| 3,873,861 | 3/1975 | Halm . |
| 4,015,154 | 3/1977 | Tanaka et al. . |
| 4,437,027 | 3/1984 | Yamamoto et al. . |
| 4,589,542 | 5/1986 | Steadman . |
| 4,720,646 | 1/1988 | Torimoto . |
| 5,020,657 | 6/1991 | Huber ...................................... 198/782 |
| 5,183,150 | 2/1993 | Chary et al. . |
| 5,213,201 | 5/1993 | Huber et al. . |
| 5,437,585 | 8/1995 | Sundseth ................................. 475/331 |
| 5,547,069 | 8/1996 | Pritchard ................................. 198/782 |
| 5,568,858 | 10/1996 | Thompson .......................... 198/781.06 |
| 5,582,286 | 12/1996 | Kalm et al. ........................ 198/781.06 |
| 5,730,274 | 3/1998 | Loomer ................................ 198/460.1 |
| 5,938,003 | 8/1999 | Huber et al. ............................. 198/782 |

FOREIGN PATENT DOCUMENTS

| | | |
|---|---|---|
| 0 355 251 A1 | 2/1990 | European Pat. Off. . |
| 0 497 045 A1 | 8/1992 | European Pat. Off. . |
| 1 956 946 | 11/1970 | Germany . |
| 39 19 613 A1 | 12/1990 | Germany . |
| 43 36 978 A1 | 5/1995 | Germany . |
| 195 39 627 A1 | 5/1996 | Germany . |
| WO 96/28719 | 9/1996 | WIPO . |

*Primary Examiner*—Christopher P. Ellis
*Assistant Examiner*—Rashmi Sharma
*Attorney, Agent, or Firm*—Knobbe, Martens, Olson & Bear, LLP

[57] ABSTRACT

A drive roller unit is provided for use in a roller drive unit for the conveyance of objects on the freight deck of an aircraft. The drive roller unit comprises a drive motor to drive a drive roller which, when in an operating position, can be brought into frictional engagement with the bottom of an object to be conveyed. A lifting mechanism with a lifting motor is used to raise the drive roller from a retracted, resting position into the raised, operating position. A control apparatus controls operation of the drive motor and the lifting motor. A differential velocity measuring means is also provided for measuring a difference between a velocity of the drive roller and a velocity of said object being conveyed to determine a slippage. The control means comprises a regulating means to which an output signal from the differential velocity measuring means is sent and which regulates the control means and thereby the drive motor and/or the lifting motor in such a way as to reduce any slippage between the drive roller and the bottom surface of said object being conveyed.

12 Claims, 2 Drawing Sheets

DRIVE ROLLER UNIT

FIELD OF THE INVENTION

The present invention relates to a drive roller unit for use in a roller drive unit for the conveyance of objects on the freight deck of an aircraft.

DESCRIPTION OF THE PRIOR ART

During the loading and unloading of aircraft, it is important that the objects to be stored in the aircraft or removed therefrom are transported into their places or out of the cargo hold as rapidly but also as reliably as possible. However, such a loading and unloading process must not only be completed in a short time, it must also take place under extremely diverse conditions. This diversity arises firstly from the configuration of the objects themselves, which may have various undersurface structures or contents of various weights, and also from the position of the aircraft or of the cargo deck, which can be tilted at various angles because the positions of parked aircraft are not always optimal and can also change depending on the weight of the load. It should also be kept in mind that the bottoms of the objects to be transported can differ in their stability and in the skid-resistance of the material of which they are made. Moisture and dirt play a major role in this regard.

Finally, the operating staff have a large role in the problems at issue here. To save costs, it is desirable to minimize the number of employees, who are furthermore often unskilled and, in particular when pressed for time, may work carelessly.

In the conventional systems it is very largely left to the operating staff to determine how conveyors such as roller drive units are controlled, and they usually work with constant conveying parameters, in particular with respect to transport speed, pressure exerted by drive rollers etc., not taking into account the variations cited above.

The object of the present invention is to provide a drive roller unit which is controlled so as to improve its traction properties, preferably to provide optimal traction properties.

SUMMARY OF THE INVENTION

According to the present invention there is provided A drive roller unit for conveying objects on the freight deck of an aircraft comprising a drive motor; a drive roller driven by the drive motor and which in an operating first position can be brought into frictional engagement with a bottom surface of an object being conveyed and located above the drive roller; a lifting motor; a lifting mechanism controlled by the lifting motor to raise the drive roller from a retracted, resting second position into the operating first position; a control means for controlling operation of the drive motor and the lifting motor; a differential velocity measuring means for measuring a difference between a velocity of the drive roller and a velocity of said object being conveyed to determine a slippage; and a regulating means to which an output signal from the differential velocity measuring means is sent and which regulates the control means and thereby the operation of at least one of the drive motor and the lifting motor to reduce any slippage between the drive roller and the bottom surface of said object being conveyed.

An important feature of the invention is that because a slippage measurement is undertaken in order to determine whether there is a differential velocity between the drive roller and the bottom surface of the object to be conveyed and as a result of this measurement operation of the drive motor and/or the lifting motor are controlled in such a way that the slippage disappears, it is thus ensured that on one hand the conveying speed is made optimal, while on the other hand the wear and tear on the drive roller is minimized. This feature increases the operating life and hence the reliability of the entire freight loading system, which is especially important with respect to the particular application of interest here.

In one embodiment of the invention the differential velocity meter preferably comprises a measurement roller with a circumferential velocity sensor, which in particular can be constructed as a rotation speed sensor. This measurement roller is brought into engagement with the bottom surface of the object to be conveyed, so that it rotates as the bottom surface passes over it.

The measurement roller can be provided separately or, as is described in greater detail below, can be mounted adjacent to the drive roller such as to rotate about the axis of rotation of the latter. In this way it is ensured that the measurement roller makes its measurement in precisely the place where the drive roller is brought into engagement with the bottom surface of the object to be conveyed.

Preferably the drive roller is subdivided into two roller components, the measurement roller being mounted between the roller components. This symmetrical construction ensures that a correct measurement signal is generated even when the object to be conveyed passes over only half of the drive roller.

The measurement roller is preferably so disposed, relative to the drive roller, that when the drive roller is raised from the resting into the operating position, the measurement roller touches the bottom surface of the object to be conveyed at a point in time before the drive roller. This can be achieved in a particularly simple manner in the case of the construction just described wherein the measurement roller is disposed so as to rotate about the axis of rotation of the drive roller, if the measurement roller is made somewhat thicker than the drive roller while its covering or its mounting has sufficient elasticity to ensure that the drive roller comes into secure engagement with the bottom of the object to be conveyed.

Preferably a force sensing means is provided to generate and send to the control apparatus a force-measurement signal dependent on a force with which the lifting motor presses the drive roller against the bottom surface of the object being conveyed. By means of such a force sensing means the lifting motor can be regulated such that the force brought to bear by the drive roller against the bottom surface of the object to be conveyed does not exceed a preset maximal force. This maximal force can be automatically or manually predetermined according to the nature of the object to be conveyed, in order to ensure optimal traction properties and also to avoid damage to the bottom of the object to be conveyed.

In one embodiment of the invention, a lifting-height sensor is also provided, by means of which the height of the drive roller at any moment can be monitored. This sensor can be used not only to move the drive roller to a predetermined height, e.g. into the retracted, resting position, but also, in connection with the force sensing means, to measure the elasticity properties, i.e. the spring constant of the bottom of the object to be conveyed, in order to predetermine a maximal load value for the engagement of the drive roller with the bottom of the object.

The regulating means is preferably so constructed that the lifting mechanism is actuated to raise the drive roller when slippage is detected. As a result, the pressure exerted by the drive roller is increased until the slippage disappears.

Preferably also, the regulating means is so constructed that when slippage is detected, the driving force or the rotation speed of the drive motor is reduced, until the slippage disappears. This procedure can be used in combination with the procedure just described.

If a force sensing means is provided to measure the pressing force, the regulating means is preferably so constructed that when the drive roller makes contact with the bottom surface of the object to be conveyed, the lifting motor is controlled in such a way as to keep the pressing force substantially constant. Hence when a container is to be conveyed, the bottom of which has an inhomogeneous stiffness, for example because of the presence of transverse pallet beams, it is ensured that the drive roller follows the profile of the loaded container bottom.

Preferably the regulating means is so constructed that when slippage is detected, first the pressing force is increased from a preset lower normal value to a predetermined higher maximal pressure, with no change in the operation of the drive motor. If slippage is still occurring when the maximal pressing force has been reached, then the rotation speed or driving force of the drive motor is reduced until no more slippage is present.

The drive roller unit is preferably controlled with reference to a predetermined set-point for the velocity with which the object is being or should be conveyed. In a manner known per se, this set-point is compared with the actual value detected by the differential velocity measuring means, so that when there is a discrepancy, the drive motor can then be regulated accordingly.

An embodiment of the present invention will be described with reference to drawings.

DESCRIPTION OF A PREFERRED EMBODIMENT

Figure 1:
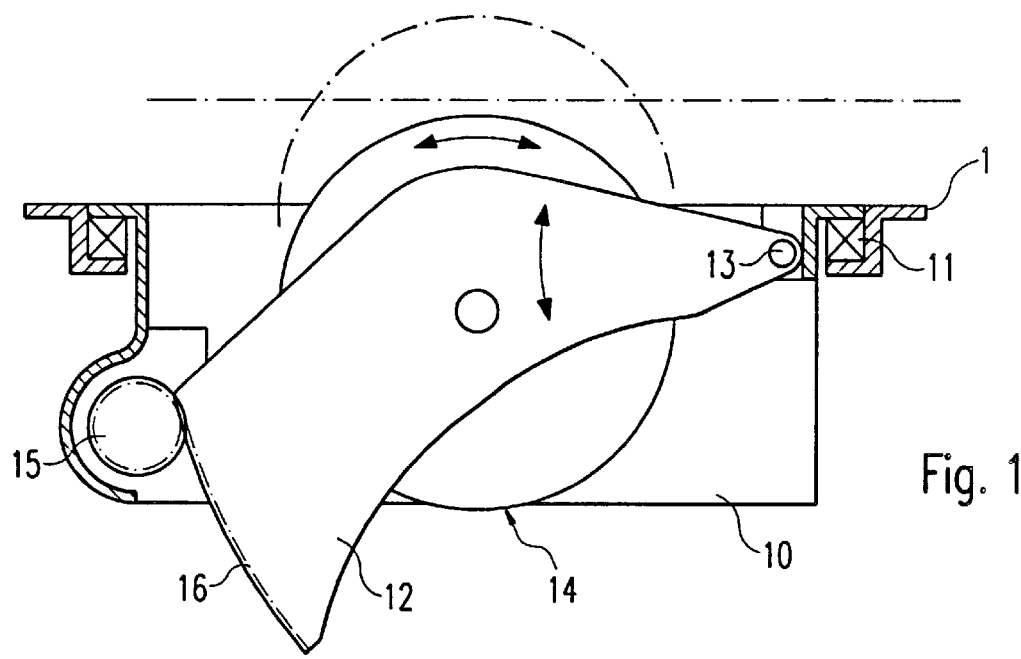
FIG. 1 is a side elevation of a drive roller unit according to the invention, in partial vertical section.

In the following description, the same reference numerals are used for identical components or equivalent components with identical functions.

Figure 2:
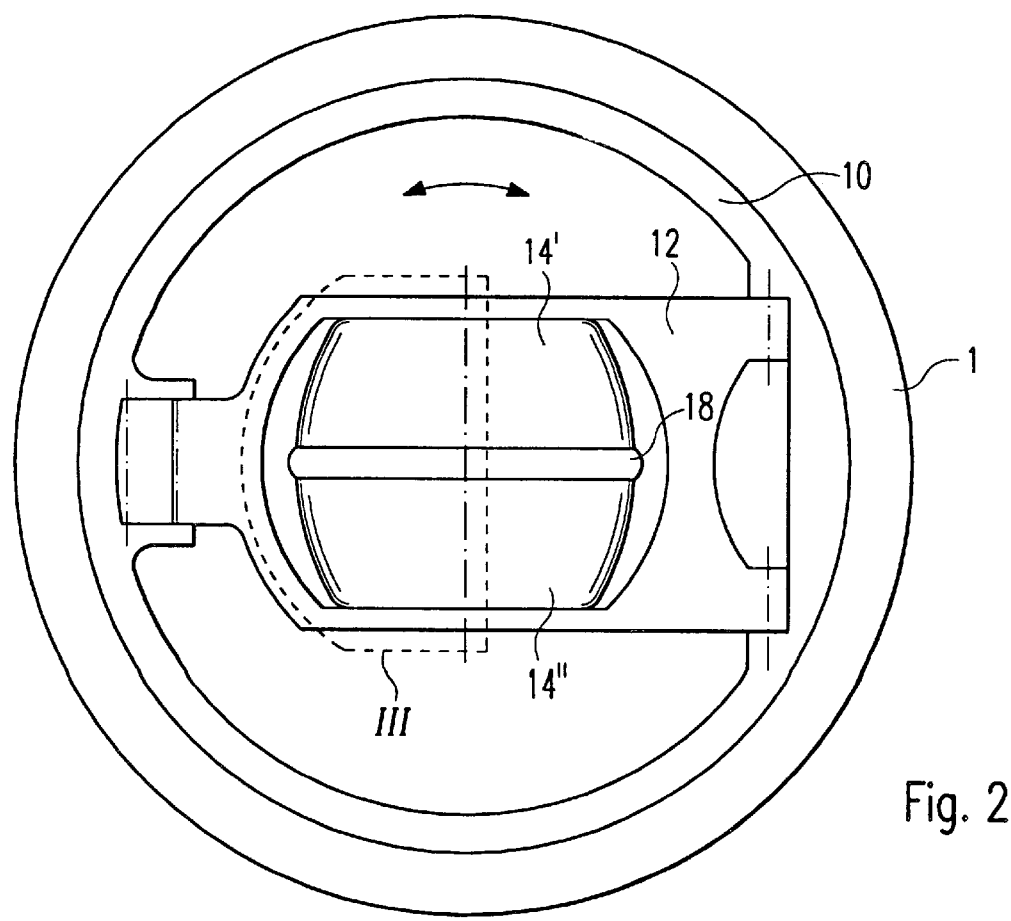
FIG. 2 is a plan view of the unit shown in FIG. 1.

In the embodiment of drive roller unit shown in FIGS. 1 and 2, a pot-shaped frame 10 is rotatably mounted in a freight deck by way of a bearing 11 and a bearing ring 1. Within the frame 10 a rocker 12 is located so that it can be rotated upwards and downwards about a pivot bolt 13 which is disposed substantially perpendicular to the rocker 12 and hence substantially parallel to the freight deck. The rocker 12 carries a drive roller 14 accommodating in its interior a drive motor by means of which it is actuated. To rotate the rocker 12, a lifting motor 15 is attached to the frame 10 and comprises a pinion that meshes with a toothed edge 16 of the rocker 12.

Figure 3:
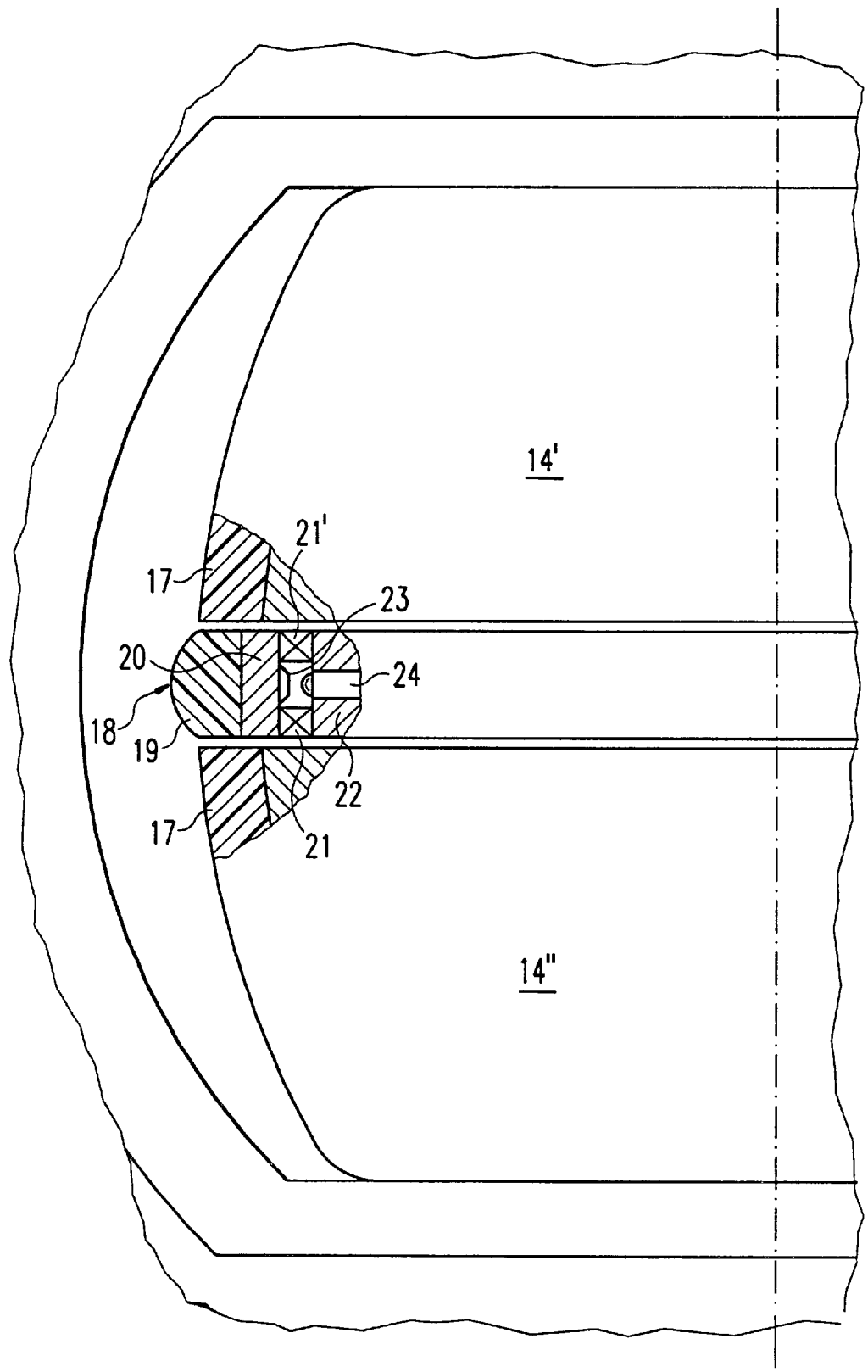
FIG. 3 is an enlarged view of a part of FIG. 2 as enclosed by the dashed line III, in partial horizontal section.

The drive roller 14, as shown in FIG. 3, is subdivided into two roller components 14' and 14", which are rigidly connected to one another and are driven by the drive motor (not shown). Each of the drive roller components 14' and 14" is provided with a friction covering 17.

Between the drive roller components 14' and 14" is mounted a measurement roller 18. The measurement roller 18 is likewise provided with a friction covering 19, which extends beyond the outer surface of the covering 17 on the drive roller components 14' and 14". The covering 19 is seated on a carrier ring 20, which is rotatably mounted on a base ring 22 by way of bearings 21 and 21'. The base ring 22 is non-rotatably connected to the rocker 12.

Uniformly distributed circumferentially over the inner surface of the carrier ring 20 are markers 23, the movement of which past a sensing mechanism 24 can be detected by the latter. In this way a rotation-speed sensor is formed.

Another rotation-speed sensor (not shown) is provided within the drive roller 14 to monitor the rotation speed or circumferential velocity of the drive roller components 14' and 14". In the pivot bolt 13 a force sensor is provided, which generates an output signal that serves as a measure of the pressing force exerted by the drive roller 14 on the bottom of an object (not shown) to be conveyed.

When an object arrives above a roller drive unit comprising a drive roller unit according to the invention, the rocker 12 is rotated by the lifting motor 15 so as to raise the drive roller 14 from a resting position (shown by the solid lines in FIG. 1) into an operating position in which the drive roller 14 or the drive roller components 14' and 14", as well as the measurement roller 18, come into engagement with the bottom of the object to be conveyed. Before the drive roller components 14' and 14" engage the bottom, the measurement roller 18 is accelerated to a degree corresponding to the velocity of the moving container.

The drive motor is controlled according to the difference between a predetermined set-point velocity of the object and its actual velocity as measured by the measurement roller 18. By means of the sensor provided in the pivot bolt 13 the pressing force is determined; it is then increased if a differential velocity between the measurement roller 18 and the drive roller components 14' and 14" is found to exist, that is if slippage is occurring. However, such a lifting of the drive roller 14 is continued only until a specified maximal force is being exerted because damage to the drive roller unit and/or to the object to be conveyed might otherwise be caused. If slippage can still be detected when this maximal value has been reached, the driving force or the rotation speed of the drive motor is adjusted downward until the slippage disappears.

In FIG. 1, the broken horizontal line indicates a "normal" position of a smooth container bottom, which position is determined by other conveying means such as passive rollers, ball mats or the like. It can be seen in this drawing that the drive roller 14 can be raised considerably above this level, in order to compensate for unevenness or curvature of the container bottom so as to optimize traction.

From the above it will be appreciated that the present invention relates not only to a drive roller unit per se but also to the way such a unit operates.

What is claimed is:

1. A drive roller unit for conveying objects on a freight deck of an aircraft comprising a drive motor;

a drive roller driven by the drive motor and which in an operating first position can be brought into frictional engagement with a bottom surface of an object being conveyed and located above the drive roller;

a lifting motor;

a lifting mechanism controlled by the lifting motor to raise the drive roller from a retracted, resting second position into the operating first position;

a control means for controlling operation of the drive motor and the lifting motor;

a differential velocity measuring means for measuring a difference between a velocity of the drive roller and a velocity of said object being conveyed to determine a slippage; and a regulating means to which an output signal from the differential velocity measuring means is sent and which regulates the control means and thereby the operation of at least one of the drive motor and the lifting motor to reduce any slippage between the drive roller and the bottom surface of said object being conveyed.

2. A drive roller unit as claimed in claim 1, wherein the differential velocity measuring means comprises a measurement roller with a circumferential velocity sensor, which measurement roller can be brought into engagement with said bottom surface of the object being conveyed.

3. A drive roller unit as claimed in claim 2, wherein the measurement roller is disposed adjacent to the drive roller and rotates about the same axis of rotation as the drive roller.

4. A drive roller unit as claimed in claim 3, wherein the drive roller is subdivided into two roller components and the measurement roller is disposed between these two roller components.

5. A drive roller unit as claimed in claim 2, wherein the measurement roller is disposed relative to the drive roller so that when the drive roller is raised from its retracted, resting second position into its operating first position, the measurement roller touches said bottom surface of the object being conveyed at a point in time before the drive roller.

6. A drive roller unit as claimed in claim 1, wherein a force sensing means is provided to generate a force-measurement signal dependent on a pressing force with which the lifting motor presses the drive roller against said bottom surface of the object being conveyed, the force-measurement signal being output to the control means.

7. A drive roller unit as claimed in claim 1, wherein the regulating means regulates the control means and thereby controls operation of the lifting motor so that the lifting mechanism is actuated to raise the drive roller when a slippage is detected.

8. A drive roller unit as claimed in claim 1, wherein the regulating means regulates the control means and thereby controls operation of the the drive motor so that the driving force of the driving motor is reduced when a slippage is detected.

9. A drive roller unit as claimed in claim 6, wherein the regulating means regulates the control means and thereby controls operation of the lifting motor so that when the drive roller is in contact with said the bottom surface of the object being conveyed, the pressing force is kept substantially constant.

10. A drive roller unit as claimed in claim 6, wherein when a slippage is detected the regulating means first regulates the control means and thereby controls operation of the lifting motor to raise the pressing force from a predetermined lower pressure to a predetermined higher maximal pressure without varying operation of the drive motor, and then after the maximal pressing force has been reached the regulating means regulates the control means and thereby controls operation of the drive motor so that the driving force of a driving motor is reduced until slippage no longer occurs.

11. A drive roller unit for conveying objects on a freight deck of an aircraft comprising a drive motor;

a drive roller driven by the drive motor and configured to be brought into an operating position in which the drive roller is in frictional engagement with a bottom surface of an object being conveyed and located above the drive roller;

a lifting motor;

a lifting mechanism controlled by the lifting motor to raise the drive roller from a retracted, resting position into the operating position;

a controller to control the drive motor and the lifting motor;

a velocity sensor measuring a difference between a first velocity of the drive roller and a second velocity of said object being conveyed to determine a slippage; and a regulator receiving an output signal from the velocity sensor, the regulator regulating the controller to modify operation of at least one of the drive motor and the lifting motor to reduce any slippage between the drive roller and the bottom surface of said object being conveyed.

12. A method of conveying objects on a freight deck of an aircraft comprising providing a roller drive unit comprising a drive roller and being installed in the freight deck of the aircraft;

controlling the drive roller between a retracted position and a raised, operating position;

frictionally engaging the drive roller in the operating position with a bottom surface of the object, located above the drive roller, to convey the object;

determining a difference between a first velocity of the drive roller and a second velocity of said object being conveyed to determine a slippage; and using the determined difference to modify operation of the drive roller to reduce any slippage between the drive roller and the bottom surface of said object being conveyed.

* * * * *